United States Patent [19]

Gerber et al.

[11] Patent Number: 4,597,666
[45] Date of Patent: Jul. 1, 1986

[54] APPARATUS FOR DETERMINING THE LIQUID WATER CONTENT OF A GAS

[75] Inventors: Hermann E. Gerber, Reston; Bernard G. Ulfers, Blacksburg, both of Va.

[73] Assignee: The United States of America as represented by the Secretary of the Navy, Washington, D.C.

[21] Appl. No.: 601,516

[22] Filed: Apr. 18, 1984

[51] Int. Cl.$^4$ ............................................. G01N 21/49
[52] U.S. Cl. ...................... 356/338; 250/574
[58] Field of Search ............... 356/336, 338, 343; 250/574

[56] References Cited

U.S. PATENT DOCUMENTS

| | | |
|---|---|---|
| 3,431,423 | 3/1969 | Keller. |
| 3,705,771 | 12/1972 | Friedman et al. ............... 356/342 X |
| 3,873,206 | 3/1975 | Wilcock. |
| 4,027,973 | 6/1977 | Kaye. |
| 4,037,964 | 7/1977 | Wertheimer et al.. |
| 4,363,551 | 12/1982 | Achter et al.. |

FOREIGN PATENT DOCUMENTS 51270 12/1972 Japan ...................... 356/338

Primary Examiner—Davis L. Willis
Assistant Examiner—Matthew W. Koren
Attorney, Agent, or Firm—Robert F. Beers; Sol Sheinbein; William R. Sharp

[57] ABSTRACT

An apparatus for determining the liquid water content (LWC) of a sample gas having water droplets suspended therein includes a light source for passing a collimated light beam through the sample gas, and a sensor for detecting the light scattered by the water droplets. The sensor includes a photodetector having a planar light sensitive surface positioned to receive scattered light. A light trap is also provided between the photodetector and the light source for blocking non-scattered light in the light beam from the photodetector. The light flux detected by the photodetector is proportional to LWC.

4 Claims, 3 Drawing Figures

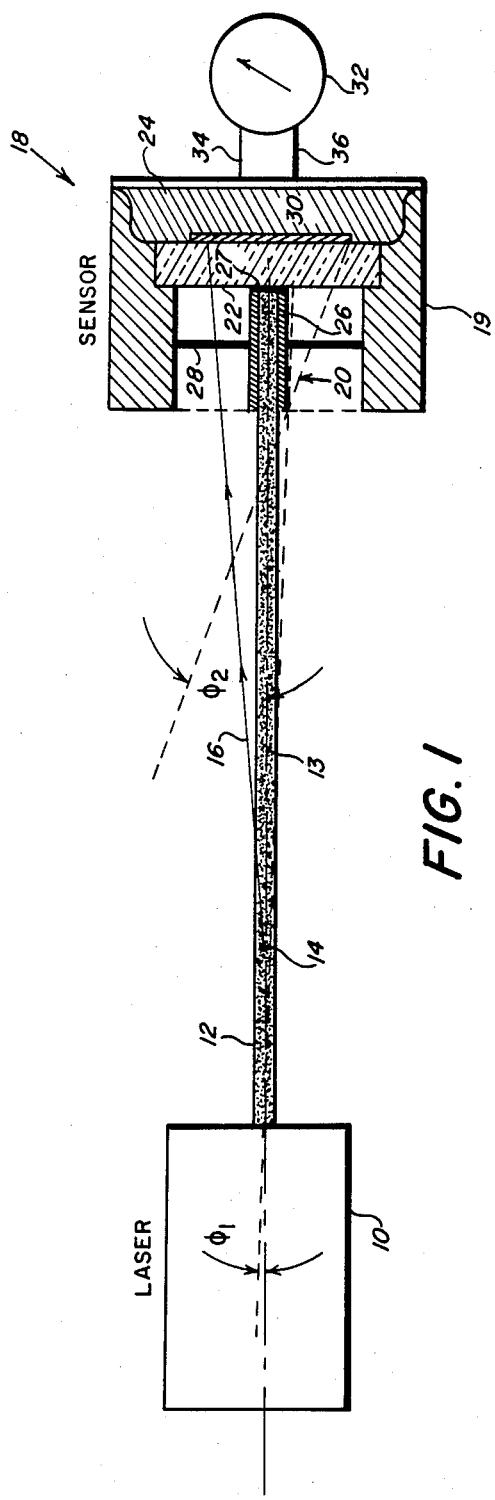
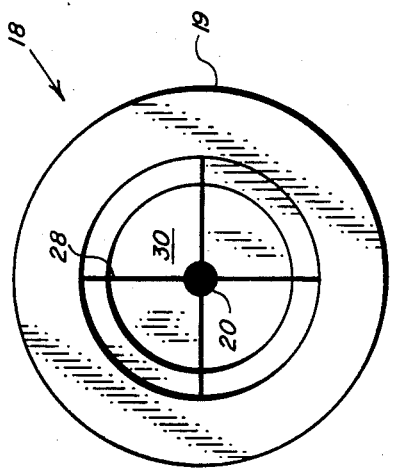

APPARATUS FOR DETERMINING THE LIQUID WATER CONTENT OF A GAS

BACKGROUND OF THE INVENTION

This invention relates to the measurement of particle content in gases, and more particularly to devices and methods for measuring the liquid water content (LWC) in a sample gas such as an atmospheric sample (i.e. clouds or fog).

LWC has been measured with various techniques, three of which will now be described. LWC is defined as the mass of liquid water per unit volume of a sample gas. In the first technique, a thin heated wire is permitted to intercept cloud or fog droplets moving by in an air stream. The heat required to keep the wire at a uniform temperature is approximately proportional to LWC. In the second method, droplets are sized with an optical particle counter and the volume of all droplets per unit atmospheric volume is summed to obtain LWC. In the third method, an optical measurement is made simultaneously on a large number of droplets to deduce LWC. This is done by measuring atmospheric light extinction using a collimated light source with a wavelength near 11 microns P. Chylek has shown that the extinction at this wavelength is proportional to LWC. Reference may be made to an article entitled "Extinction and Liquid Water Content of Fogs and Clouds" in *J. Atmos. Sci.*, Vol. 35. pp. 296–300 for an extensive discussion of Chylek's technique.

Various disadvantages in the above described techniques are typical in prior devices and methods for measuring LWC. For example, the first method has a limited threshold for smaller water droplets (i.e. below 2 microns in diameter). The second and third methods of measuring LWC described above require complex and expensive instrumentation. In particular, the third method of Chylek requires the use of infrared light, and thus requires the use of expensive optical components. In addition, method three relies on light extinction and requires a relatively lengthy device. The size of such a device is critical in many situations, for example in an airplane, where space limitations exist.

SUMMARY OF THE INVENTION

It is, therefore, an object of the present invention to provide an apparatus for measuring LWC which will detect very small (i.e. less than 2 microns in diameter) water droplets suspended in a sample.

It is also an object of this invention to provide an LWC measuring device which is relatively simple and inexpensive.

It is a further object of the present invention to provide an apparatus for measuring LWC which is relatively small in size.

The above objects are realized in an apparatus for measuring LWC in a sample gas having liquid water droplets suspended therein which utilizes a light source for passing a collimated beam along an optical axis, causing some of this light to be scattered, and a sensor for detecting the total flux of the scattered light over a certain region described below. This region lies in a plane which intersects the light beam such that an area in the plane is intersected by the light beam, wherein the region is continuous, closed, and totally surrounds the area. Scattered light directed toward the region is herein defined as regional scattered light. The sensor detects the total flux of substantially all of the regional scattered light. Furthermore, a volume in space, which is illuminated along the entire length of the light beam between the light source and sensor, is totally occupied by the sample gas. The flux detected by the sensor in the above described arrangement is proportional to the LWC of the sample gas.

In the preferred embodiment, the sensor includes a photodetector having a planar light sensitive surface which is coplanar with, and which occupies the same area as the above described region. The sensor also includes a light trap positioned between the light source and sensor for receiving nonscattered light in the light beam so as to block the nonscattered light from the light sensitive surface of the photodetector.

An apparatus for measuring LWC constructed according to the present invention will detect droplets as small as about 0.2 microns in diameter. In addition, the apparatus does not depend on the use of infrared wavelengths as in the Chylek device. Thus, the complex and expensive infrared optical components are not necessary in the present invention. Finally. an apparatus according to the present invention may be miniaturized to a light source-sensor separation of about 1 to 2 feet. This feature can become very important where space limitations exist.

BRIEF DESCRIPTION OF THE DRAWINGS

FIG. 1 is a cross-sectional view of one embodiment of the present invention.

FIG. 2 is an end view of a sensor employed in the FIG. 1 embodiment.

DESCRIPTION OF THE PREFERRED EMBODIMENT

Figure 3:
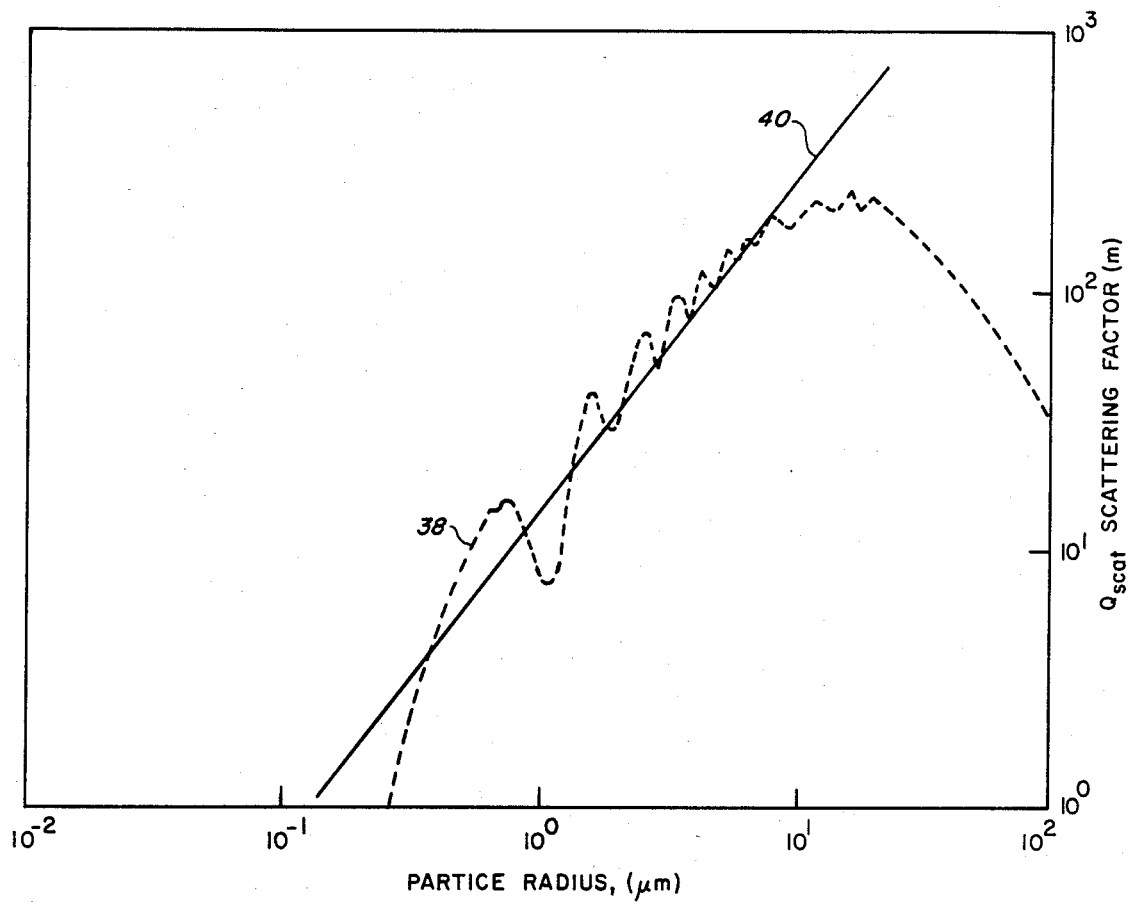
FIG. 3 is a log-log graph of scattering factor $Q'_{scat}$ as a function of particle radius for illuminated water droplets.

An apparatus for determining LWC in a sample gas is described herein which utilizes a light source for passing a collimated beam through the sample gas, and a sensor for detecting the flux of light scattered by water droplets suspended in the sample gas. The detected light flux is proportional to LWC.

Referring now to FIG. 1, there is shown a cross-sectional view of one embodiment of the present invention. Laser 10, which may be, by way of example, a helium neon laser, produces a collimated light beam 12 having an optical axis 13 which passes through a sample gas having suspended water droplets therein. These water droplets illuminated by the beam 12 are schematically represented by dots, as shown at 14. Some of the light in beam 12 incident on such a representative water droplet 14 is scattered by refraction, internal reflection, and diffraction. A scattered light ray is shown at 16.

It should be understood that laser 10 could be replaced by any light source which can produce a highly collimated light beam. For example, an incandescent source of light could be employed in combination with collimating lenses.

A sensor is provided in the illustrated embodiment, as shown generally at 18, which includes housing 19, light trap 20, interference filter 22, and photodetector 24. Sensor 18 acts to produce an output proportional to the LWC as will be explained below. Both sensor 18 and laser 10 may be mounted on a base (not shown). Typically, the distance between laser 10 and sensor 18 is between about 1 foot and 2 feet. Additionally, if LWC of an atmospheric sample is being measured, the space between laser 10 and sensor 18 is simply left open to ambient air. In any case, light beam 12 between laser 10 and light trap 20 illuminates along its entire length a volume in space which is totally occupied by the sample gas.

Light trap 20 comprises a tube 26 positioned within housing 19 such that the axis of tube 26 is aligned with optical axis 13. As shown, tube 26 has a closed end 27 which receives beam 12 and blocks beam 12 from propagating beyond the trap. Preferably, tube 26 is painted on its inner surface with black paint to more effectively absorb light within the tube, and thus enhance its effectiveness as a trap. The diameter of tube 26 should be selected so that nearly all of beam 12 falls within and is trapped by the tube. The fraction of beam 12 which is not trapped by tube 26 should be sufficiently small so as not to mask the scattered light from the droplets. An acceptable fraction, for example, would be equal to the fraction of the scattered light which corresponds to the smallest desired LWC measurement. Such as acceptable fraction is about 0.0001. Pins 28 are provided to mount tube 26 as described above so as to intercept beam 12. In the illustrated embodiment, one end of an individual pin 28 is mounted within housing 19, and the other end is mounted within the wall of tube 26. As should be understood by one skilled in the art, pins 28 are provided solely to support tube 26 in the desired position, and perform no other function in device operation.

As shown, interference filter 22 is mounted within housing 19 so as to receive scattered light. Filter 22 is typically a conventional narrow band filter which filters out all wavelengths but the wavelength of the beam 12. Consequently, filter 22 allows essentially only light scattered from beam 12 to be incident on photodetector 24, thus preventing erroneous readings resulting from stray light. Such a filter is commerically available from Oriel Co. of Stamford, Conn. It should also be understood that the use of this filter is not critical to device operation. However, to achieve accurate measurements, some means should be employed to shield photodector 24 from stray light. For example device components could be mounted in a closed, essentially light tight container if some means is provided to fill the space between laser 10 and sensor 18 with the sample gas. An additional alternative might be simply operating the device in a darkened environment, at night for example.

Photodetector 24, which may be, for example, a large area photomultiplier, is mounted in housing 19 immediately behind filter 22 such that light trap 20 lies between it and laser 10. Photodetector 24 includes a light sensitive surface 30 which is larger in diameter than the diameter of light trap 20. Thus, light sensitive surface 30 receives and detects substantially all of the light scattered toward it. In the illustrated embodiment, the only fraction of scattered light directed toward light sensitive surface 30 which does not reach this surface is that fraction intercepted by pins 28, which are as small as possible so as to limit this fraction. Thus, as noted above, substantially all of the scattered light scattered toward light sensitive surface 30 is detected by the light sensitive surface. Ideally, one would like to have no elements intercepting scattered light, as long as some means is provided to support light trap 20 in the desired position so as to block and absorb nonscattered light.

The total light flux incident on light sensitive surface 30 is proportional to the LWC of the sample gas as will be explained in more detail below. Photodetector 24 produces an output signal proportional to the light flux falling on its light sensitive surface. Therefore, the output signal of photodetector 24 is proportional to LWC. A meter 32, such as a voltmeter, is provided to receive and measure the above mentioned output signal via leads 34 and 36. The meter reading is therefore proportion 1 to the LWC of the sample gas. As an alternative to the type of meter shown in FIG. 1, any appropriate readout equipment could be used, such as a digital indicator or recorder.

Although a photodetector of the type which produces a signal in response to light incident thereon is utilized in the illustrated embodiment, it should be understood that other types of photodetectors could be used. For example, a photodiode (i.e. RCA C-30810) could be employed which changes in resistance in response to incident light. In this sort of arrangement, the photodiode would be supplied with a current, and the voltage across the photodiode monitored.

Angles $\phi_1$ and $\phi_2$ shown in FIG. 1 will now be defined and their significance explained. $\phi_2$ is defined as that angle formed between the optical axis 13 and a line intersecting the outer edge of tube 26 and intersecting the point of the light sensitive surface outer periphery farthest from the optical axis. In this particular illustrated embodiment, light sensitive surface 30 is circular, so that any point on the outer periphery is a point farthest from the optical axis 13. $\phi_1$ is defined as that angle formed between a line intersecting the point from which the light beam originates from laser 10 and also intersecting the outer edge of tube 26. The accuracy of the readout on meter 32 will deteriorate as the angular range $\phi_2$-$\phi_1$ increases. This angular range relates to the field of view of photodetector 24 with respect to the scattered light. More specifically, it is preferred that $\phi_2$-$\phi_1$ be no more than about 10 degrees and $\phi_1$ not more than about 0.5 degrees in order to preserve a high degree of accuracy.

Referring now to FIG. 2, there is shown an end view of sensor 18. Illustrated are housing 19, light trap 20, pins 28, and light sensitive surface 30. As shown, in this particular embodiment light sensitive surface 30 is circular.

An explanation for the proportional relationship of scattered light detected in the present invention and LWC will now be given through a mathematical analysis. In this analysis, a device constructed according to the FIG. 1 embodiment will be considered. Such a device as explained above includes a planar light sensitive surface and a light trap. The irradiance of an elemental area of the sensor by light scattered by the droplets is given by $$H = \int N(\phi) \sin \theta \, d\omega, \qquad (1)$$

where $\phi$ is the scattering angle, $\theta$ is the angle formed between the light sensitive surface plane and a line drawn between a point on the above mentioned plane and the front edge of the trap, and $d\omega = d\phi dx/y \sec \theta$. In this analysis, the light sensitive surface has an x-y axis therein, wherein the origin is at the point where the optical axis intersects the plane of the surface. The radiance in the volume dv of the beam is given by $$N(\phi) = i \, \beta'(\phi) dv/da, \text{ where} \qquad (2)$$

$$da = dx dL \cos \theta, \text{ and} \qquad (3)$$

$$dv = ds\, dL, \quad (4)$$

where i is the irradiance of the aerosols by the light beam with a radiant flux I, da is the horizontal area of the volume dv projected in the direction of the elemental area of the sensor, dL is the length of the area da, dx is the width and ds is the cross section of the beam, dω is the solid angle subtended by the area of the volume dv at the sensor, and $$\beta'(\phi) = \frac{1}{k^2} \int \left( \frac{i_1 + i_2}{2} \right) n(r) dr \quad (5)$$

is the volume scattering function for a polydispersion, where $k = 2\pi/\lambda$, $i_1$ and $i_2$ are the Mie intensity functions, and r is the radius of an individual droplet.

The area of the sensor (light sensitive surface) is $$\int dA = 2\pi \int y\, dy, \quad (6)$$

and the total scattered-light flux incident on the sensor is $$F = \int H\, dA \quad (7)$$

Multiplying the integrand in (7) by $r^2/r^2$, noting that $\sin \theta = \cos \phi$, and combining (1)–(7) gives $$F = \pi I \int_{r_1}^{r_2} \int_{\phi_1}^{\phi_2} \int_{y_1}^{y_2} \frac{r^2}{a^2} (i_1 + i_2) \cos\phi\, n(r)\, dr\, d\phi\, dy, \quad (8)$$

which holds for unpolarized light, and for the assumption that the light beam is one dimensional. The integration limits for $\phi$ are depicted in FIG. 1, those for r encompass the range of particle radii expected in the particle size distributions, $y_2$ is set to equal the radius of the light sensitive surface, and $y_1$ is set to equal the radius of the light trap.

By defining a scattering factor $$Q'_{scat}(\lambda, r) = 1/a^2 \int \int (i_1) \cos\phi\, d\phi\, dy, \quad (9)$$

which applies to the geometry of FIG. 1, expressing the liquid water content W in terms of n(r), the size distribution of the droplets, and $\rho$, the droplet density as follows $$W = 4/3\pi P \int r^3 n(r) dr, \quad (10)$$

and by combining (8) with (10) yields $$W = \frac{4\rho}{3I} \frac{\int r^3 n(r)\, dr}{\int Q'_{scat}(\lambda, r) r^2 n(r)\, dr} F. \quad (11)$$

$Q'_{scat}$ may be plotted as a function of particle radius as shown in FIG. 3 for a wavelength of 0.6328 m. The curve obtained is shown at 38. A fitted straight line 40 may be drawn through curve 38. The slope, herein denoted as $c_2$, of line 40 is positive and is about 45°, indicating a linear relationship between $Q'_{scat}$ and r for a given range of r. Thus, for this range $Q'_{scat}$ may be approximated by the linear relationship $$Q'_{scat} \approx c_2 r. \quad (12)$$

The oscillations in the $Q'_{scat}$ curve of FIG. 3 play a minimal role in the deviation of (12) from linearity, since the integration of W in (11) is done for a spectrum of r values which smooths the effect of the oscillations.

Combining (11) and (12) cancels the particle size dependence, and gives $$W \approx \frac{4\rho F}{3c_2 I}.$$

Thus, in a device constructed according to the present invention, the liquid water content W is approximately proportional to the detected light flux.

An alternate embodiment, not shown, of the present invention could employ a collecting lens positioned in front of a photodetector for collecting and focusing the scattered light onto the photodetector. In this type of arrangement, there is no need for the diameter of the photodetector's light sensitive surface to be larger than that of the light trap. Instead, the dimensions of the lens should be similar to that of the light sensitive surface in the FIG. 1 embodiment.

Thus, there is provided by the present invention an apparatus for determining the liquid water content (LWC) of a sample gas wherein light scattered by suspended droplets in the gas is detected to give a reading proportional to LWC. An apparatus constructed according to the present invention is relatively inexpensive, since it does not require expensive infrared optical components. Additionally, the apparatus will detect very small droplets (i.e. 0.2 microns), and can be miniaturized to meet stringent space limitations. All of the above mentioned features are lacking in prior art LWC measuring devices.

Obviously many modifications and variations of the present invention are possible in light of the above teachings. It is therefore to be understood that within the scope of the appended claims the invention may be practiced otherwise than as specifically described.

What is claimed is:

1. An apparatus for determining the liquid water content of a sample gas having liquid water droplets suspended therein comprising:

a light source means passing a collimated light beam along an optical axis through the sample gas, some of the light in the light beam being forward scattered by the suspended water droplets, wherein in a plane intersecting the light bean an area of the plane is intersected by the light beam;

a region lying in said plane which intersects the light beam such that said area in the plane is intersected by the light beam, said region being continuous and closed, and wherein said region totally surrounds the area, the scattered light directed toward said region being denoted as regional scattered light;

sensor means positioned along the optical axis for detecting the total flux of substantially all of the regional scattered light, including a photodetector having a planar light sensitive surface which is coplanar with, and which occupies the same area as said region, said sensor means also incliduing a light trap means comprising a tube whose axis is aligned with the optical axis, said tube having two ends, wherein one of said ends is closed such that nonscattered light in the light beam incident on the closed end is blocked from said photodetector and the end of said tube closest to said light source means has an outer edge, said light sensitive surface having an outer periphery such that a line intersecting the outer edge of said tube and intersecting the point of said light sensitive surface outer periphery farthest from the optical axis forms an angle $\theta_2$ with respect to the optical axis, and wherein a line intersecting the point from which the light beam originates from said light source means and also intersecting said outer edge of said tube forms an angle $\theta_1$ with respect to the optical axis, wherein $\theta_2-\theta_1$ is not more than about 10 degrees and $\theta_1$ is not more than about 0.5 degrees, positioned along the optcal axis between said light source means and said photodetector so as to receive nonscattered light in the light beam, said light trap means blocking the nonscattered light from being incident on said light sensitive surface of said photodetector, wherein the nonscattered light in the light beam between said light source means and said sensor means illuminates along its entire length a volume in space, the volume in space being totally occupied by the sample gas, whereby said detected total flux is proportional to the liquid water content of the sample gas.

2. An apparatus for determining the liquid water content of a sample gas having liquid water droplets suspended there in comprising:
a light source means comprising a laser for passing a collimated light beam along an optical axis through the sample gas, some of the light in the light beam being forward scattered by the suspended water droplets, wherein in a plane intersecting the light beam an area of the plane is intersected by the light beam;
a region lying in said plane which intersects the light beam such that said area in the plane is intersected by the light beam, said region being continuous and closed, and wherein said region totally surrounds the area, the scattered light directed toward said region being denoted as regional scattered light,
sensor means positioned along the optical axis for detecting the total flux of substantially all of the regional scattered light, including a photodetector having a planar light sensitive surface which is coplanar with, and which occupies the same area as said region, said sensor means also including a light trap means comprising a tube whose axis is aligned with the optical axis, said tube having two ends, wherein one of said ends is closed such that nonscattered light in the light beam incident on the closed end is blocked from said photodetector and the end of said tube closest to said laser has an outer edge, said light sensitive surface having an outer periphery such that a line intersecting the outer edge of said tube and intersecting the point of said light sensitive surface outer periphery farthest from the optical axis forms an angle $\theta_2$ with respect to the optical axis, and wherein a line intersecting the point from which the light beam originates from said laser and also intersecting said outer edge of said tube forms an angle $\theta_1$ with respect to the optical axis, wherein $\theta_2-\theta_1$ is no more than about 10 degrees and $\theta_1$ is not more than about 0.5 degrees, positioned along the optical axis between said light source means and said photodetector so as to receive nonscattered light in the light beam, said light trap means blocking the nonscattered light from being incident on said light sensitive surface of said photodetector, wherein the nonscattered light in the light beam between said light source means and said sensor means illuminates along its entire length a volume in space, the volume in space being totally occupied by the sample gas, whereby said detected total flux is proportional to the liquid water content of the sample gas.

3. An apparatus as recited in claim 2, wherein the distance between said sensor means and said laser as measured along the optical axis is between about 1 and about 2 feet.

4. An apparatus for determining the liquid water content of a sample gas having liquid water droplets suspended therein comprising:
a laser for passing a collimated light beam along an optical axis through the sample gas, some of the light in the light beam being forward scattered by the suspended water droplets;
a light trap which comprises a tube having two ends positioned along the optical axis so as to receive nonscattered light in the light beam, one end of said tube being closed such that that nonscattered light incident on the closed end is blocked from passing beyond said tube, and wherein the end of said tube closest to said laser has an outer edge, and also wherein the light beam between said laser and said light trap illuminates along its entire lengths a volume in space being totally occupied by the sample gas;
a photodetector having a planar light sensitive surface positioned such that said light sensitive surface intersects the optical axis, said photodetector also being positioned such that said light trap is between said laser and said photodetector such that said light sensitive surface receives and detects the flux of substantially all of the light scattered toward said light sensitive surface, wherein said light sensitive surface has as outer periphery such that a line intersecting the outer edge of said tube and intersecting the point of said light sensitive surface outer periphery farthest from the optical axis forms an angle $\phi_2$ with respect to the optical axis, and wherein a line intersecting the point from which the light beam originates from said laser and also intersecting the outer edge of said tube forms an angle $\phi_1$ with respect to the optical axis, the angular range $\phi_2-\phi_1$ being no more than about 10 degrees. and $\phi_1$ being no more than about 0.5 degrees;
whereby the detected light flux is proportional to the liquid water content of the sample gas.

* * * * *